United States Patent [19]

Bortolin et al.

[11] Patent Number: 5,011,961
[45] Date of Patent: Apr. 30, 1991

[54] METHOD OF MAKING ORGANOSILBUTADIYNE POLYMERS

[75] Inventors: Roberto Bortolin, Barry, Italy; Bhukandas Parbhoo, Midland, Mich.

[73] Assignee: Dow Corning Limited, Barry, Wales

[21] Appl. No.: 537,843

[22] Filed: Jun. 13, 1990

[51] Int. Cl.$^5$ .................................. C07F 7/08
[52] U.S. Cl. ........................................ 556/431
[58] Field of Search ............................. 556/431

[56] References Cited

U.S. PATENT DOCUMENTS

| | | | |
|---|---|---|---|
| 3,758,541 | 9/1973 | Chandra et al. | 556/431 |
| 4,814,472 | 3/1989 | Lau | 556/431 |
| 4,921,989 | 5/1990 | Ishihara et al. | 556/431 |

OTHER PUBLICATIONS

Chwary et al., "J.A.C.S.", 95, No. 10, 1973, pp. 3324–3330.
West et al., "J.A.C.S.", 93, No. 7, 1971, pp. 1720–1724.

*Primary Examiner*—Paul F. Shaver
*Attorney, Agent, or Firm*—Roger E. Gobrogge

[57] ABSTRACT

Organosilbutadiyne polymers having the general formula $R'-[(R)_2Si-C\equiv C-C\equiv C]_n-(R)_2SiR'$ wherein R is a hydrogen atom, a hydrocarbon group or a substituted hydrocarbon group, R' is hydroxyl, halogen or R and n is an integer, are made by (A) reacting $HC\equiv C-C\equiv CH-OZ$ with alkyllithium in a molar ratio of 1:3 wherein Z denotes an alkyl group having up to 6 carbon atoms followed by (B), further reacting the product of (A) with one or more dihalosilanes.

8 Claims, No Drawings

METHOD OF MAKING ORGANOSILBUTADIYNE POLYMERS

This invention relates to a method of making organosilbutadiyne polymers.

According to the invention there is provided a method of making polymers having the general formula $R'-[(R)_2Si-C\equiv C-C\equiv C)]_n-(R)_2SiR'$, wherein R denotes a hydrogen atom, a hydrocarbon group or a substituted hydrocarbon group, R' denotes hydroxyl, halogen or R and n denotes an integer which comprises (A) reacting $HC\equiv C-CH=CH-OZ$ with alkyllithium in a molar ratio of 1:3 wherein Z denotes an alkyl group having up to 6 carbon atoms, followed by (B) further reacting the product of (A) with one or more dihalosilanes.

In the method of the invention Z is preferably a methyl group. 1-methoxybut-1-en-3-yne is commercially available.

The alkyl group in the alkyllithium compound is preferably a lower alkyl group for example methyl, ethyl or n-butyl.

The dihalosilanes are known substances many of which are commercially available. Preferably the dihalosilane is a dichlorosilane. The other substituents of the dihalosilanes may be hydrogen, a hydrocarbon group or a substituted hydrocarbon group, for example alkyl, e.g. methyl, ethyl, hexyl, dodecyl or octadecyl, aryl, e.g. phenyl or naphthyl, alkenyl, e.g. vinyl, allyl or hexenyl, tolyl or styryl. Preferably these substituents are alkyl or aryl. The most preferred dihalosilane is dimethyldichlorosilane, diphenyldichlorosilane or methylphenyldichlorosilane.

The reaction may be carried out in the presence of a solvent which is a hydrocarbon solvent or an ether solvent, for example tetrahydrofuran, diethyl ether, hexane or toluene. Preferably the reaction mixture is kept below ambient temperature, i.e. below about 20° C. during the reaction steps (A) and (B), but ambient or higher temperatures are also allowed. Suitable temperatures may range from −30° C. upwards. Step (B) of the reaction may be carried out in the same vessel as step (A), preferably under the same reaction conditions as step (A). Both steps may be carried out in the presence of the same solvent, for example by adding the dihalosilane to the reaction product of step (A).

It is preferred to use a slight stoichiometric excess of the dihalosilane in order to ensure the reaction of step (B) runs to completion. A mixture of dihalosilanes may be used which will result in the production of polymers having a mixture of silicon-bonded substituents. Upon completion the reaction mixture is neutralised for example in an aqueous buffer solution with a pH value around 5, e.g. of ammoniumchloride. The reaction product is usually purified by extracting or volatilising the solvent, washed and filtered. Yields of more than 80% of the theoretical value have been achieved, in some cases even more than 90%.

The polymers obtained by the method of the invention have useful optical and electronic properties arising from their electron-rich nature. The polymers may be used as semiconductor materials or in waveguide technology. Due to the acetylenic unsaturation the polymers may also serve as intermediates for further reaction, for example addition reaction with compounds having silicon-bonded hydrogen atoms. The latter compounds may bear certain functional groups which would thus be linked to the polymers produced by the method of the invention. Polymers made by the method of the invention are structurally pure materials. They can also be melted and thus shaped and moulded prior to any conversion into silicon carbide if desired.

There now follows an example in which all parts are expressed by weight unless otherwise mentioned.

EXAMPLE

To a solution of 7.93 g of 1-methoxybut-1-en-3-yne in 100 ml tetrahydrofuran, cooled to −25° C., was added 100 ml of a solution of 2.9M butyllithium. The resulting suspension was stirred for 1 hour at that temperature. Then 18.72 g of dimethyldichlorosilane was added and the mixture was stirred for a further 2 hours at the same temperature followed by 4 hours at ambient temperature. After this the reaction mixture was poured into a saturated aqueous solution of $NH_4Cl$. The organic phase was separated and the aqueous phase extracted with 50 ml of diethylether. The extract was mixed with the organic phase and washed with 50 ml of water. After drying the mixture over $Na_2SO_4$ it was filtered and the solvent evaporated. 150 ml of methanol was added to the residue to give a white precipitate, which was again filtered and dried under reduced pressure. 8.7 g of a product was obtained which was characterised by $C^{13}$, $Si^{29}$ Nuclear Magnetic Resonance and infrared as $HO[(CH_3)_2Si-C\equiv C-C\equiv C)]_n(CH_3)_2SiOH$ wherein n denotes a value of about 16 as was determined by Size Exclusion Chromatography (polystyrene standard). The yield was 85% of the theoretical value.

That which is claimed is:

1. A method of making polymers having the general formula $R'-[(R)_2Si-C\equiv C-C\equiv C]_n(R)_2SiR'$ wherein R is selected from the group consisting of hydrogen, hydrocarbon groups and substituted hydrocarbon groups, R' is selected from the group consisting of a hydroxyl group, halogen atoms, hydrogen, hydrocarbon groups and substituted hydrocarbon groups and n denotes an integer greater than 1 comprising (A) reacting $HC\equiv C-C=CH-OZ$ with allkyllithium in a molar ratio of 1:3 wherein Z denotes an alkyl group having up to 6 carbon atoms followed by (B), further reacting the product of (A) with one or more dihalosilanes.

2. A method according to claim 1 wherein Z is methyl.

3. A method according to claim 1 wherein the alkyl group in alkyllithium is a lower alkyl.

4. A method according to claim 1 wherein the dihalosilane is a dichlorosilane.

5. A method according to claim 4 wherein the dichlorosilane is selected from the group consisting of dimethylchlorosilane, diphenyldichlorosilane and methylphenyldichlorosilane.

6. A method according to claim 1 which is carried out in the presence of a solvent.

7. A method according to claim 1 whereby the temperature of the reaction mixture in both steps (A) and (B) is kept below 20° C.

8. A method according to claim 1 whereby a stoichiometric excess of the dihalosilane is used.

* * * * *